United States Patent [19]
White

[11] Patent Number: 5,662,656
[45] Date of Patent: Sep. 2, 1997

[54] INSTRUMENTATION AND METHOD FOR DISTAL FEMORAL SIZING, AND ANTERIOR AND DISTAL FEMORAL RESECTIONS

[75] Inventor: Stephen E. White, Cordova, Tenn.

[73] Assignee: Wright Medical Technology, Inc., Arlington, Tenn.

[21] Appl. No.: 569,711

[22] Filed: Dec. 8, 1995

[51] Int. Cl.⁶ .................................................. A61B 17/56
[52] U.S. Cl. ............................. 606/88; 606/86; 606/87
[58] Field of Search .................................. 606/86, 87, 88

[56] References Cited

U.S. PATENT DOCUMENTS

| | | | |
|---|---|---|---|
| 4,567,886 | 2/1986 | Petersen | 606/88 |
| 4,722,330 | 2/1988 | Russell et al. | 606/88 |
| 4,759,350 | 7/1988 | Dunn et al. | |
| 5,037,423 | 8/1991 | Kenna | 606/88 |
| 5,129,909 | 7/1992 | Sutherland | |
| 5,342,368 | 8/1994 | Petersen | 606/88 |
| 5,364,401 | 11/1994 | Ferrante et al. | 606/88 |
| 5,423,827 | 6/1995 | Mumme et al. | 606/87 |
| 5,454,816 | 10/1995 | Ashby | 606/88 |
| 5,486,178 | 1/1996 | Hodge | 606/88 |

FOREIGN PATENT DOCUMENTS

| | | | |
|---|---|---|---|
| 380451 | 8/1990 | Italy | 606/88 |

OTHER PUBLICATIONS

*Total Condylar & Posterior Stabilized Surgical Technique, Ortholoc® Advantim™*, Wright Medical Technology, Inc., 1993.

*Primary Examiner*—Michael Buiz
*Assistant Examiner*—Julian W. Woo
*Attorney, Agent, or Firm*—Walker, McKenzie & Walker, P.C.

[57] ABSTRACT

Instrumentation for and a method of sizing the end of a distal femur, and resecting the distal femur. An instrument body construct is provided with an instrument body and a valgus module for attachment to the instrument body. The instrument body construct has a distal aspect abutting surface with a planar face for abutting the distal aspect of a distal femur at a fixed angle to the longitudinal axis of the distal femur, having a posterior aspect abutting surface with a planar face for abutting the posterior aspect of the distal femur, and having a passageway therethrough. An anterior feeler gauge is provided for attachment to the instrument body construct and for contacting a portion of the anterior aspect of the distal femur to indicate the anterior-to-posterior size of the distal femur. A resection guide is provided for attachment to the instrument body construct for guiding a bone resection tool to resect the distal femur. The resection guide may have a first position for guiding the bone resection tool to perform an anterior femoral resection and a second position for guiding the bone resection tool to perform a distal femoral resection.

8 Claims, 5 Drawing Sheets

INSTRUMENTATION AND METHOD FOR DISTAL FEMORAL SIZING, AND ANTERIOR AND DISTAL FEMORAL RESECTIONS

BACKGROUND OF THE INVENTION

1. Field of the Invention

The present invention relates, in general, to instrumentation for and a method of sizing a distal femur and guiding a bone resection tool to make anterior and distal femoral resections.

2. Information Disclosure Statement

In order to implant a distal femoral prosthesis on a distal femur, certain substantially "standard" steps are taken. One of the initial steps is to accurately size the distal femur to assist the surgeon in selecting the proper prosthesis size. Other steps include a plurality of resections or cuts made to the end of the distal femur to prepare the end of the distal femur to receive the prosthesis. These resections or cuts may include: (1) a distal femoral resection to remove a portion of the distal surface or end of the distal femur substantially equal to the thickness to be replaced by the distal condyle of the prosthesis unless special ligament problems dictate otherwise, etc.; (2) an anterior femoral resection to remove a portion of the anterior aspect of the distal femur; (3) an anterior bevel resection or resections to remove an angular portion of the distal femur between the distal femoral resection and the anterior femoral resection; (4) a posterior resection or resections to remove a portion of the posterior surface of the distal femur; (5) a posterior bevel resection or resections to remove an angular portion of the distal femur between the distal femoral resection and the posterior resection; (6) a patellar track groove cut to create or enhance the shallow groove in the femoral patellar groove to accommodate a recessed patellar track of a femoral prosthesis; and (7) a posterior stabilized cut or cuts to create a cavity for receiving the housing of a posterior stabilized femoral prosthesis.

Surgical techniques and instrumentation for preparing a distal femur to receive a distal implant prosthesis are disclosed in the document, *Total Condylar & Posterior Stabilized Surgical Technique, ORTHOLOC® ADVANTIM™*, Wright Medical Technology, Inc. (1993). As disclosed therein, multiple steps are taken to prepare a distal femur to receive a distal femoral prosthesis. In general, the steps start with preoperative planning to estimate the size of the prosthesis needed by comparing a lateral radiograph of the distal femur with an implant template. The template size that most closely matches the profile of the distal femur on the anterior and posterior aspect is normally chosen. If full length extremity films are available, the appropriate valgus angle may be estimated by the angle formed between the anatomical axis (the longitudinal axis of the femoral shaft) and the mechanical axis (a line extending between the centers of the femoral head, the knee joint, and the ankle joint). The knee joint can then be exposed and a femoral sizing caliper used to confirm the size estimate made during preoperative templating as disclosed at page 5 of the *Total Condylar & Posterior Stabilized Surgical Technique, ORTHOLOC® ADVANTIM™* publication. The femoral sizing caliper is extended and placed flush over the distal femur with the posterior aspect of the caliper positioned against the posterior condyles, with a moveable anterior gauge positioned against the anterior cortex, and with a feeler gauge rod positioned parallel to the longitudinal axis of the femoral shaft with its indicator point resting directly on bone that is clear of any tissue. The proper implant size can then be read from the face of the caliper. A distal femoral cut guide is positioned on the distal femur and a distal femoral resection is made using an oscillating saw as disclosed at pages 7–9 of the *Total Condylar & Posterior Stabilized Surgical Technique, ORTHOLOC® ADVANTIM™* publication. The distal femoral cut guide is then removed and an anterior/posterior (A/P) bevel cut guide is seated flush against the distal femoral cut using bone clamps and/or nails, Steinmann pins, etc., and an anterior condyle or flange resection is made using a wide saw blade and the A/P bevel cut guide as disclosed at pages 11–12 of the *Total Condylar & Posterior Stabilized Surgical Technique, ORTHOLOC® ADVANTIM™* publication. A medial anterior bevel resection is made using a wide saw blade and the A/P bevel cut guide, a lateral anterior bevel resection is made using the a saw blade and the A/P bevel cut guide, a medial posterior bevel resection is made using a narrow saw blade and the A/P bevel cut guide, a lateral posterior bevel resection is made using the narrow saw blade and the A/P bevel cut guide, a medial posterior condyle resection is made using the narrow saw blade and the A/P bevel cut guide, and a lateral posterior condyle resection is made using the narrow saw blade and the A/P bevel cut guide as disclosed at pages 11–12 of the *Total Condylar & Posterior Stabilized Surgical Technique, ORTHOLOC® ADVANTIM™* publication. The A/P bevel cut guide is then removed and a patellar track positioner is fixed to the distal femur to guide a cutting tool, such as a powered patellar track burr, to cut or resect a patellar track groove in the distal femur to accommodate the recessed patellar track of the final femoral implant prosthesis as disclosed at page 18 of the *Total Condylar & Posterior Stabilized Surgical Technique, ORTHOLOC® ADVANTIM™* publication. If it is desired to implant a posterior stabilized femoral prosthesis, a posterior stabilized endmill guide is secured to the patellar track positioner, and a posterior stabilized endmill cutter is then used with the posterior stabilized endmill guide to cut or resect a posterior stabilized cut in the distal femur to accommodate the posterior stabilized housing as disclosed at pages 42–43 of the *Total Condylar & Posterior Stabilized Surgical Technique, ORTHOLOC® ADVANTIM™* publication. A housing punch may be used with the posterior stabilized endmill guide to remove any remaining bone posterior to the endmill cut. Alternatively, a rongeur or saw may also be used after the posterior stabilized endmill guide is removed.

Dunn et at., U.S. Pat. No. 4,759,350, issued Jul. 26, 1988, discloses a system of instruments for preparing a distal femur to receive a distal implant prosthesis. The Dunn et al. system includes a distal femoral cutting guide 65 shown in FIGS. 7 and 8 thereof that is mounted to an alignment guide 40 after an anterior femoral cutting guide 55 has been used to cut through the anterior condyles 51 to create a flattened area on the distal femur, and after the anterior femoral cutting guide 55 has been removed from the alignment guide 40.

Sutherland, U.S. Pat. No. 5,129,909, issued Jul. 14, 1992, discloses an apparatus and method for making precise bone cuts in a distal femur. The Sutherland apparatus and method is used after a femoral cutting block (not shown) has first been used to guide an oscillating saw to accomplish a distal femoral resection by removal or resection of the distal condyles to provide planar surfaces on the distal femoral.

None of these patents or references disclose or suggest the present invention. That is, none of these patents or references disclose or suggest instrumentation or a method for sizing the end of a distal femur and then guiding a bone resection tool to make anterior and/or distal femoral resections. More specifically, none of these patents or references disclose or suggest instrumentation for or a method of mounting an instrument body construct including an instrument body and a valgus module on the distal end of an intramedullary rod with a portion of the construct resting against the unresected distal aspect of a distal femur and with another portion of the construct resting snugly against the posterior aspect of the distal femur; mounting an anterior feeler gauge on the construct and adjusting the assembly so the anterior feeler gauge contacts a portion of the anterior aspect of the end of the distal femur to thereby measure the anterior-posterior size of the distal femur; mounting a resection guide on the construct; and then using the resection guide to guide a bone resection tool to make anterior and/or distal femoral resections.

SUMMARY OF THE INVENTION

The present invention provides instrumentation for and a method of sizing a distal femur, guiding a bone resection tool to make an anterior femoral resection on that distal femur, and guiding the bone resection tool to make a distal femoral resection on that distal femur. A basic concept of the present invention is to provide an instrument and method that can works in concert with a straight intramedullary rod; that establishes the appropriate valgus angle, external rotation, anterior-to-posterior femoral size of a distal femur; and that with a single attachment provides a guide for both anterior and distal femoral resections.

The instrumentation of the present invention includes, in general, a construct including an instrument body and a valgus module for attachment to the instrument body, the construct having a distal aspect abutting surface for abutting the distal aspect of a distal femur with the plane of the distal aspect abutting surface positioned at a fixed angle to the longitudinal axis of the distal femur, a posterior aspect abutting surface for abutting the posterior aspect of the distal femur, and a cavity therethrough; an anterior feeler gauge for attachment to the instrument body and for contacting a portion of the anterior aspect of the distal femur to indicate the anterior-to-posterior size of the end of the distal femur; and a resection guide for attachment to the instrument body and for guiding a bone resection tool to perform anterior and/or distal femoral resections.

The method of the present invention includes, in general, the steps of implanting an intramedullary rod in the distal femur with the distal end of the intramedullary rod extending from the distal femur; providing instrumentation including an anterior feeler gauge, a resection guide, and an instrument body construct including an instrument body and a valgus module for attachment to the instrument body; the instrument body construct having a distal aspect abutting surface with a planar face for abutting the distal aspect of a distal femur, having a posterior aspect abutting surface with a planar face for abutting the posterior aspect of the distal femur, and having a passageway therethrough for receiving the distal end of an intramedullary rod to position the planar face of the distal aspect abutting surface at a fixed angle to the longitudinal axis of the intramedullary rod; inserting the passageway of the valgus module over the distal end of the intramedullary rod until the distal aspect abutting surface of the instrument body abuts the distal aspect of the distal femur; mounting the anterior feeler gauge on the instrument body construct; adjusting the instrument body construct and anterior feeler gauge until the posterior aspect abutting surface of the instrument body construct abuts the posterior aspect of the distal femur and until the anterior feeler gauge engages the anterior aspect of the distal femur; mounting the resection guide on the instrument body construct in a first position and using the resection guide to guide a bone resection tool to perform an anterior femoral resection of the distal femur; and mounting the resection guide on the instrument body construct in a second position and using the resection guide to guide the bone resection tool to perform a distal femoral resection of distal femur.

DESCRIPTION OF THE PREFERRED EMBODIMENT

The preferred embodiment of the instrumentation of the present invention is shown in FIGS. 1–8, 11–13 and 15–18, and identified by the numeral 11. The instrumentation 11 is used in conjunction with a distal femur 13 and a bone resection tool 15 such as a typical oscillating saw or the like having a bone resection member 16 such as a saw blade or the like to make a distal femoral cut or resection 17 by removing a thickness or amount of bone from the distal aspect or surface 19 of the distal femur 13, and to make an anterior femoral cut or resection 21 to remove a thickness or amount of bone from the anterior aspect or surface 23 of the distal femur 13.

The instrumentation 11 has an instrument body construct 25 including an instrument body 27 and a valgus module for attachment to the instrument body 27. The instrument body construct 25 has a distal aspect abutting surface 29 preferably with a planar face portion 30 for abutting the distal aspect or surface 19 of the distal femur 13 at a fixed angle to the longitudinal axis 14 of the distal femur 13, has a posterior aspect abutting surface 31 preferably with a planar face portion 32 for abutting the posterior aspect or surface 33 of the distal femur 13, and has a passageway therethrough. The passageway is especially designed for receiving the distal end 35 of an intramedullary rod 37 in such a manner so as to position the planar face portion 30 of the distal aspect abutting surface 29 at a fixed angle to the longitudinal axis 39 of the intramedullary rod 37. When the intramedullary rod 37 is properly implanted in the distal femur 13, the longitudinal axis 39 thereof will be aligned with the longitudinal axis 14 of the distal femur 13.

The instrument body 27 preferably includes a first body member 41 having a first end 43 and a second end 45, and a second body member 47 having a first end 49 and a second end 51. The first and second body members 41, 47 are preferably movably attached to one another to allow the distance between the first end 43 of the first body member 41 and the second end 51 of the second body member 47 to be varied. Thus, the first and second body members 41, 47 are preferably slidably joined to one another to allow the distance between the first end 43 of the first body member 41 and the second end 51 of the second body member 47 to be easily increased or decreased. The first body member 41 may have a pair of opposed grooves 53 therein and the second body member 47 may have a pair of opposed ridges 55 for slidably receiving the grooves 53 of the first body member 41 in a manner that allows the first and second body members 41, 47 to slide relative to one another so that the distance between the first end 43 of the first body member 41 and the second end 51 of the second body member 47 can be easily increased or decreased as will now be apparent to those skilled in the art.

The first body member 41 preferably has a paddle 57 attached to and extending outward from the first end 43 there. The paddle 57 has an abutting or contact surface 59 for abutting or contacting the posterior aspect 33 of the distal femur 13 and for defining or forming the posterior aspect abutting surface 31 of the instrument body construct 25. The paddle 57 is preferably shaped and sized so that the abutting surface 59 thereof will typically substantially abut the posterior femoral condyles at the posterior aspect 33 of the distal femur 13. The paddle 57 may be generally U-shaped when viewed from one end, etc.

The instrument body construct 25 preferably includes a group of graduated valgus modules for providing a graduated sequence of valgus angles. More specifically, the instrument body construct 25 preferably includes a first valgus module 61, a second valgus module 63, and a third valgus module 65. Each valgus module 61, 63, 65 has a cavity 67 therethrough for receiving the distal end 35 of the intramedullary rod 37 and for defining, at least in part, the passageway through the instrument body construct 25. The cavity 67 through each valgus module 61, 63, 65 has a longitudinal axis 69 that forms an angle 71 with a plane 73 that is substantially perpendicular to the planar face portion 30 of the distal aspect abutting surface 29 of the instrument body construct 25 when a specific valgus module 61, 63, 65 is attached to the instrument body 27. The angle 71 is based on the valgus angle of a specific patient's femur and may vary substantially within the range of ±15° or so. The group of valgus modules 61, 63, 65 is preferably designed to cover the most common or typical valgus angles. Thus, the first valgus module 61 may be designed with a ±3° valgus angle, the second valgus module 63 may be designed with a ±5° valgus angle, and the third valgus module 65 may be designed with a ±7° valgus angle. Each valgus module 61, 63, 65 is preferably reversibly attached to the instrument body 27 to provide valgus angles for both left and right legs. Thus, for example, the first valgus module 61 is preferably attachable to the instrument body 27 in a first position so that the angle 71 is +3°, and is preferably attachable to the instrument body 27 in a second position so that the angle 71 is −3°, thereby providing a 3° valgus angle for either a right or left leg. Likewise, the second valgus module 63 is preferably attachable to the instrument body 27 in a first position so that the angle 71 is +5°, and is preferably attachable to the instrument body 27 in a second position so that the angle 71 is −5°, thereby providing a 5° valgus angle for either a right or left leg. Similarly, the third valgus module 65 is preferably attachable to the instrument body 27 in a first position so that the angle 71 is +7°, and is preferably attachable to the instrument body 27 in a second position so that the angle 71 is −7°, thereby providing a 7° valgus angle for either a right or left leg.

While the specific construction of the valgus modules may vary, each valgus module 61, 63, 65 preferably has a barrel portion 75 and an outwardly extending flange 77 at one end of the barrel portion 75, and the instrument body 27 preferably has a slot 79 therethrough for slidably receiving the barrel portion 75 of one of the valgus modules 61, 63, 65. The slot 79 is preferably elongated to allow limited slidable adjustment of a valgus module 61, 63, 65 between the first end 43 of the first body member 41 and the second end 51 of the second body member 47. The slot 79 is preferably formed or defined by a first slot 81 through the first body member 41 and a second slot 83 through the second body member 47 that align with one another with the first and second body members 41, 47 are movably attached to one another.

The instrumentation 11 preferably includes a lock member 85 for locking a selected valgus module 61, 63, 65 to the instrument body 27. The lock member 85 may consist of a lock nut 87 for screwing onto an externally threaded portion 89 of the barrel portion 75 of each valgus module 61, 63, 65 in such a manner to clamp the instrument body 27 between the flange 77 of a selected valgus module 61, 63, 65 and the lock nut 87. The lock nut 87 is preferably adapted to allow it to be easily tightened and loosened by hand, etc.

The instrumentation 11 includes an anterior feeler gauge 91 attachable to the instrument body construct 25 for contacting a portion of the anterior aspect 23 of the distal femur 13. The anterior feeler gauge 91 preferably includes an elongated, L-shaped stylus 93 having a pointed end 95 for contacting the anterior aspect 23 of the distal femur 13. The anterior feeler gauge 91 preferably includes a base member 97 for attaching the stylus 93 to the instrument body construct 25. The base member 97 preferably includes a head 99 having an aperture 101 therethrough for slidably receiving the shaft portion of the stylus 93, and preferably includes a trunk portion 103 for attachment to the instrument body construct 25. While the specific construction of the means for attaching the stylus 93 to instrument body construct 25, may vary, the trunk portion 103 may have external threads 105 thereon and the second end 51 of the second body member 47 of the instrument body construct 25 may have a threaded aperture 107 therein for screwably receiving the trunk portion 103 of the base member 97 thereby attaching the stylus 93 to the instrument body construct 25.

The distance between the planar face portion 32 of the posterior aspect abutting surface 31 (i.e., the abutting surface 59 of the paddle 57) and the pointed end 95 of the stylus 93 is preferably adjustable to allow the anterior-to-posterior size of the end of the distal femur 13 to be measured and indicated. That is, the distance between the planar face portion 32 of the posterior aspect abutting surface 31 (i.e., the abutting surface 59 of the paddle 57) and the pointed end 95 of the stylus 93 is or indicates the anterior-to-posterior size of the end of the distal femur 13. The anterior-to-posterior size of the end of distal femur 13 can thus be determined or measured by moving the planar face portion 32 of the posterior aspect abutting surface 31 (i.e., the abutting surface 59 of the paddle 57) and the pointed end 95 of the stylus 93 toward from one another until the planar face portion 32 of the posterior aspect abutting surface 31 (i.e., the abutting surface 59 of the paddle 57) firmly abuts or contacts the posterior aspect 33 of the distal femur 13 and until the pointed end 95 of the stylus 93 firmly abuts or contacts the anterior aspect 23 of the distal femur 13.

The specific construction of the means for varying the distance between the planar face portion 32 of the posterior aspect abutting surface 31 (i.e., the abutting surface 59 of the paddle 57) and the pointed end 95 of the stylus 93 may vary. For example, the stylus 93 may be adjustably attached to the instrument body construct 25 in a manner which allows the pointed end 95 thereof to be moved toward and away from the paddle 57, etc. However, in the preferred embodiment of the instrumentation 11, varying the distance between the first end 43 of the first body member 41 and the second end 51 of the second body member 47 by sliding the first and second body members 41, 47 toward and away from one another causes the pointed end 95 of the stylus 93 to be moved toward and away from the paddle 57 as will now be apparent to those skilled in the art. The instrument body 27 preferably has a scale 109 that indicates the distance between the pointed end 95 of the stylus 93 and the planar face portion 32 of the posterior aspect abutting surface 31 (i.e., the abutting surface 59 of the paddle 57), and thus indicates the anterior-to-posterior size of the end of the distal femur 13. The scale 109 may include graduated markings or indicia 111 on the first body member 41 which can be aligned with the first end 49 of the second body member 47 to provide the appropriate measurement as will now be apparent to those skilled in the art.

Figure 1:
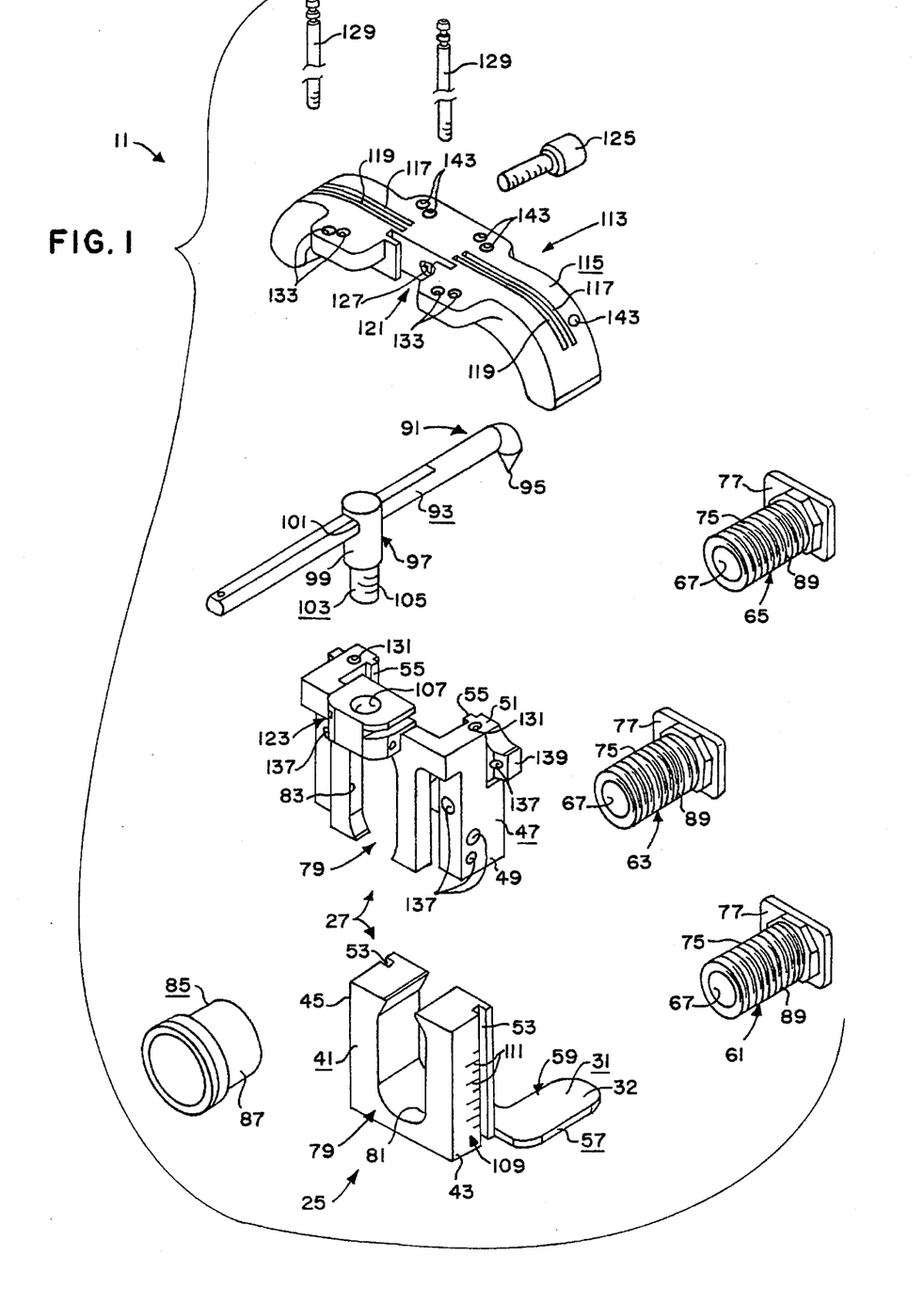
FIG. 1 is an exploded perspective view of the instrumentation of the present invention.
Figure 2:
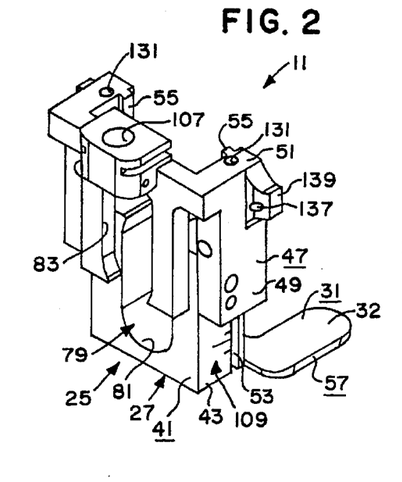
FIG. 2 is a perspective view of an instrument body of the instrumentation of the present invention.
Figure 3:
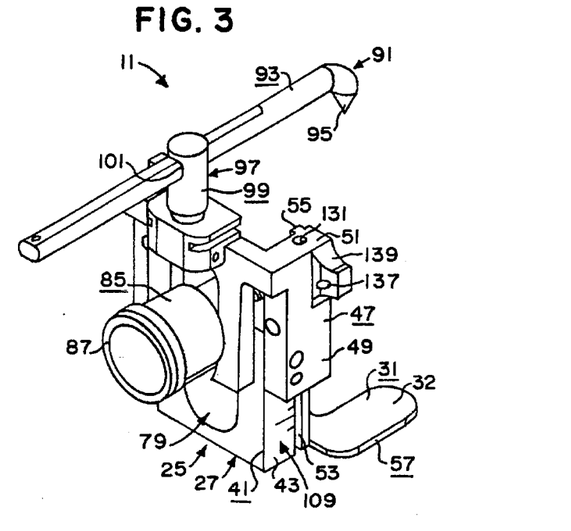
FIG. 3 is a perspective view of the instrument body of FIG. 2 combined with a valgus module and an anterior feeler gauge of the instrumentation of the present invention.
Figure 4:
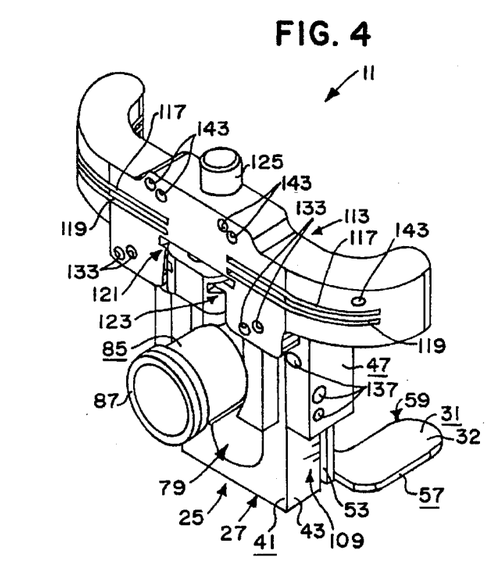
FIG. 4 is a perspective view of the instrument body of FIG. 2 combined with a valgus module and a resection guide of the instrumentation of the present invention with the resection guide positioned for an anterior femoral resection.
Figure 5:
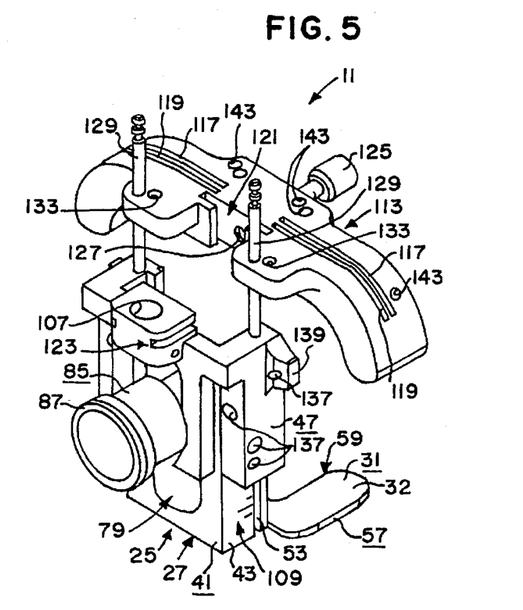
FIG. 5 is a perspective view of the instrument body of FIG. 2 combined with a valgus module and a resection guide of the instrumentation of the present invention with the resection guide positioned for a distal femoral resection.
Figure 6:
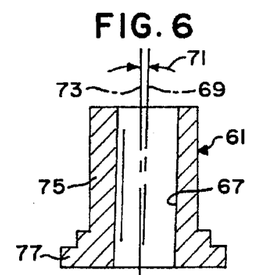
FIG. 6 is a sectional view of a first valgus module of the instrumentation of the present invention.
Figure 7:
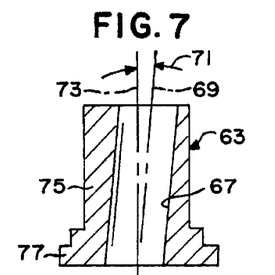
FIG. 7 is a sectional view of a second valgus module of the instrumentation of the present invention.
Figure 8:
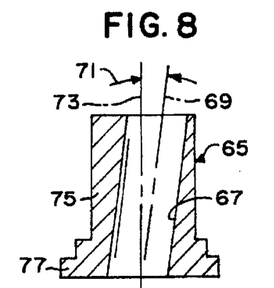
FIG. 8 is a sectional view of a third valgus module of the instrumentation of the present invention.
Figure 9:
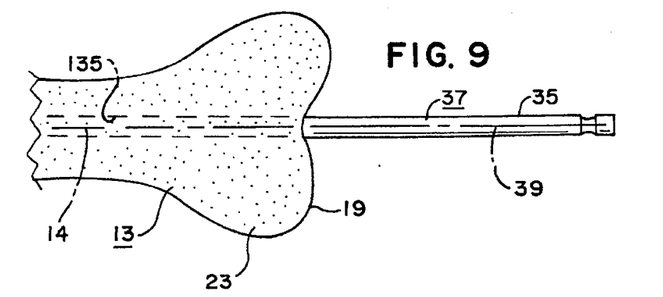
FIG. 9 is a somewhat diagrammatic anterior view of a distal femur having an intramedullary rod implanted therein.
Figure 10:
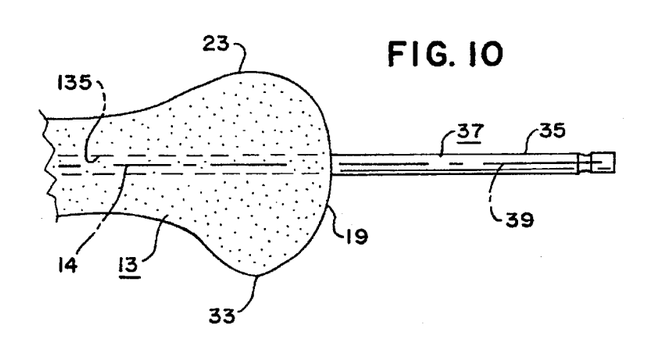
FIG. 10 is a somewhat diagrammatic lateral view of a distal femur having an intramedullary rod implanted therein.
Figure 11:
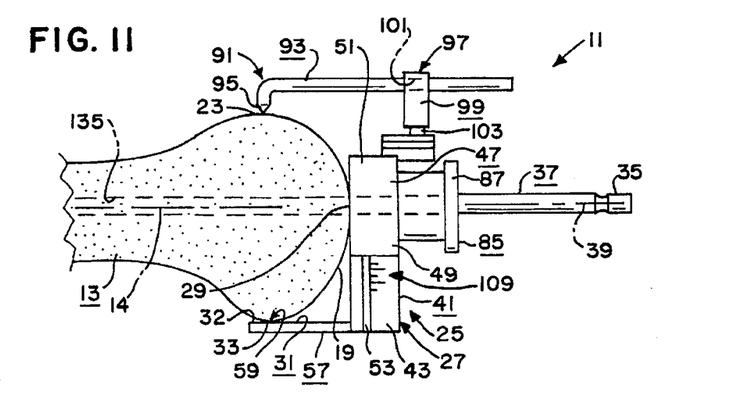
FIG. 11 is a somewhat diagrammatic lateral view of a distal femur having an intramedullary rod implanted therein, combined with an instrument body, a valgus module and an anterior feeler gauge of the instrumentation of the present invention.
Figure 12:
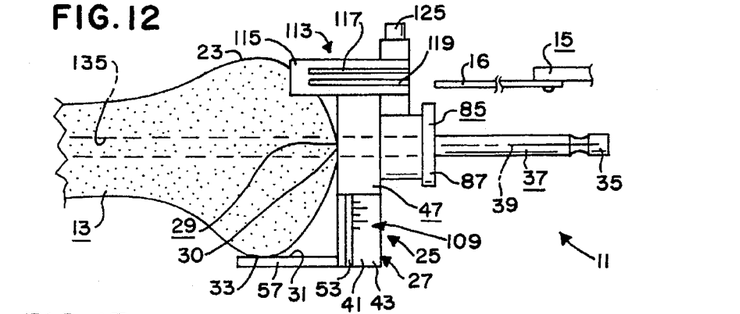
FIG. 12 is a somewhat diagrammatic lateral view of a distal femur having an intramedullary rod implanted therein, combined with an instrument body, a valgus module and a resection guide of the instrumentation of the present invention with the resection guide positioned for an anterior femoral resection, and showing a bone resection tool for making an anterior femoral resection of the distal femur.
Figure 13:
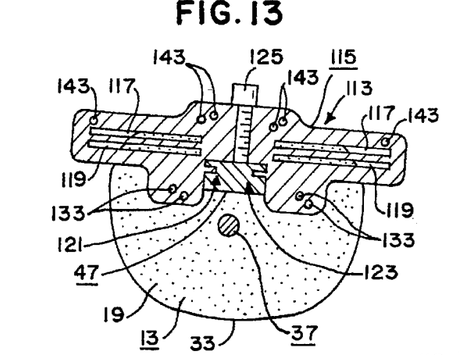
FIG. 13 is a somewhat diagrammatic transverse sectional view of a FIG. 12 with portions thereof omitted for clarity.
Figure 14:
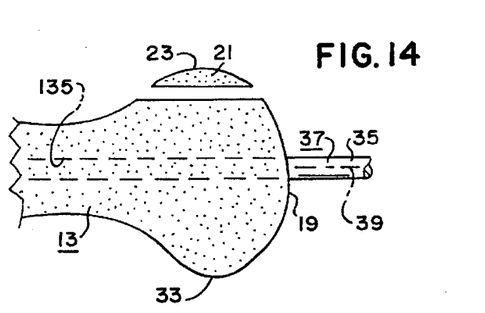
FIG. 14 is a somewhat diagrammatic lateral view of a distal femur having an intramedullary rod implanted therein, showing an anterior femoral resection thereof.
Figure 15:
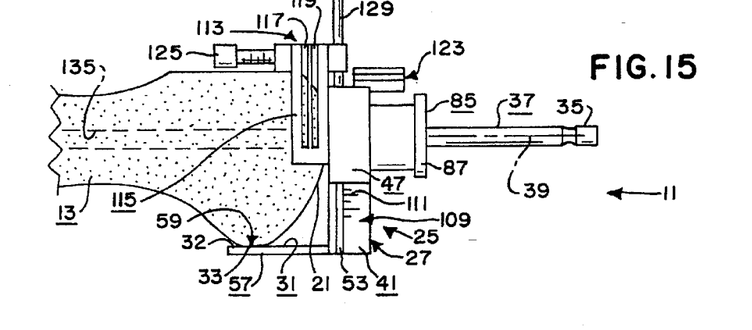
FIG. 15 is a somewhat diagrammatic lateral view of a distal femur having an intramedullary rod implanted therein, combined with an instrument body, a valgus module and a resection guide of the instrumentation of the present invention with the resection guide positioned for a distal femoral resection.
Figure 16:
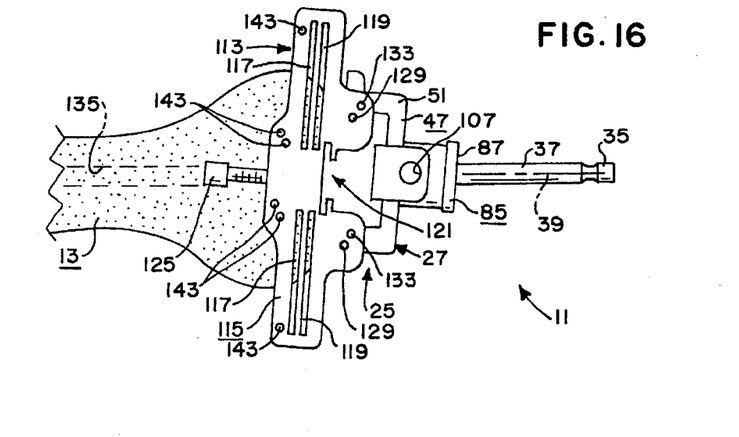
FIG. 16 is a somewhat diagrammatic anterior view of FIG. 15.
Figure 17:
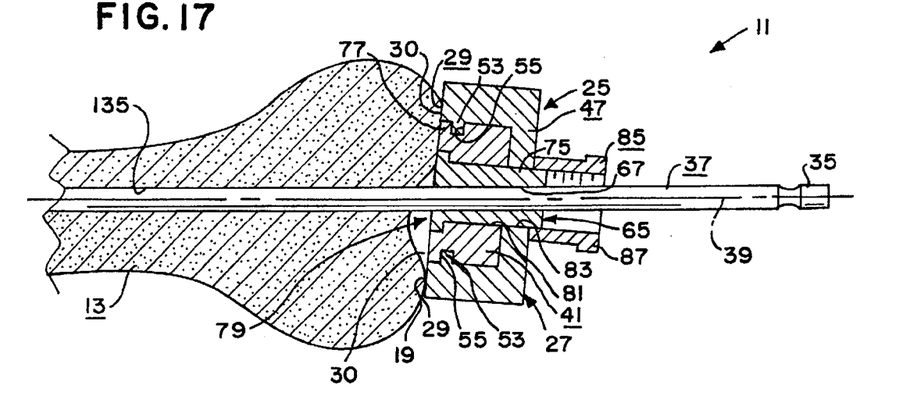
FIG. 17 is a somewhat diagrammatic anterior sectional view of FIG. 15 with portions thereof omitted for clarity.
Figure 18:
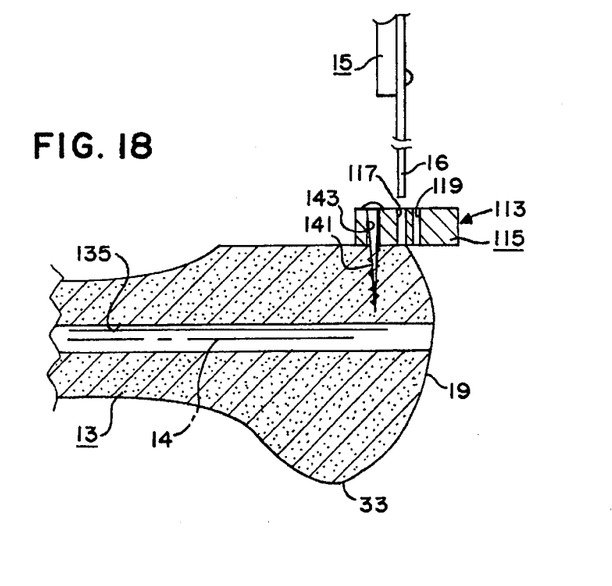
FIG. 18 is a somewhat diagrammatic lateral sectional view of FIG. 15 with portions thereof omitted, and showing a bone resection tool for making a distal femoral resection of the distal femur.
Figure 19:
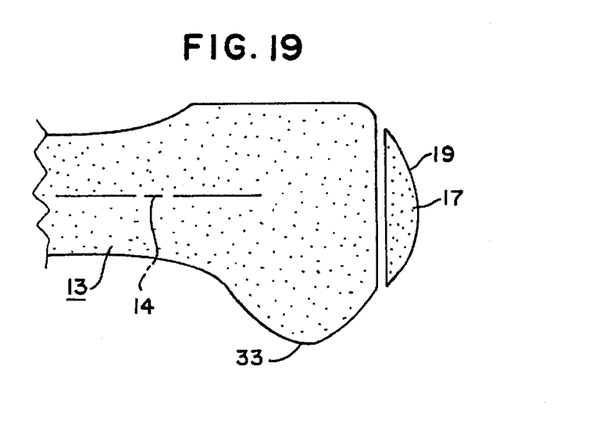
FIG. 19 is a somewhat diagrammatic lateral view of a distal femur after an anterior femoral resection thereof, showing a distal femoral resection thereof.

The instrumentation 11 includes a resection guide 113 attachable to the instrument body construct 25 for guiding the bone resection tool 15 to perform an anterior femoral resection 21 of the end of the distal femur 13 and a distal femoral resection 19 of the end of the distal femur 13. The resection guide 113 preferably includes a body member 115 having at least one and preferably a first slot 117 and a second slot 119 therethrough for guiding the bone resection member 16 of the bone resection tool 15 to make a precise, planar resection through the distal femur 13. The resection guide 113 is adapted to be attached to the instrument body construct 25 in a first position as shown in FIGS. 12 and 13 to orient the slots 117, 119 therethrough to guide the bone resection tool 15 to perform an anterior femoral resection 21 of the end of the distal femur 13, and is attachable to the instrument body construct 25 in a second position as shown in FIGS. 15, 16 and 18 to orient the slots 117, 119 therethrough to guide the bone resection tool 15 to perform a distal femoral resection 17 of the end of the distal femur 13. The body member 115 may include structure defining a T-slot 121 or the like for receiving a corresponding T-flange 123 of the second body member 47 of the instrument body 27 in a manner to position the resection guide 113 in the first position. A lock screw 125 is preferably provided for screwing through a threaded cavity 127 in the body member 115 of the resection guide 113 and against a portion of the second body member 47 of the instrument body 27 when the T-slot 121 of the body member 115 is positioned on the T-flange 123 of the body member 47 for thereby locking the resection guide 113 to the instrument body construct 25 in the first position. The instrumentation 11 is preferably designed so that the slots 117, 119 will be automatically set to guide the bone resection member 16 of the bone resection tool 15 to make a precise, planar resection through the distal femur 13 with a precise external rotation. For example, the T-flange 123 of body member 47 may be angled in such a manner so that when the T-slot 121 of the body member 115 of the resection guide 113 is slid thereon, the slots 117, 119 will be positioned at a 3° degree angle with respect to the frontal plane of the distal femur 13 as clearly shown in FIG. 13, to thereby automatically set the anterior resection at 3° of external rotation. A pair of pins 129 are preferably provided for locking the resection guide 113 to the instrument body construct 25 in the second position. More specifically, the second body member 47 of the instrument body 27 may have a pair of apertures 131 for receiving the pins 129 and the body member 115 of the resection guide 113 may have a plurality of spaced apertures 133 therethrough for allowing the pins 129 to extend therethrough in a manner to position the resection guide 113 in the second position. The plurality of apertures 131 allows the relative position of the resection guide 113 with respect to the instrument body construct 25 to be varied depending on whether the instrumentation 11 is being used for a right or left knee, etc.

The instrumentation 11 can be manufactured in various specific sizes and designs, out of various specific materials, and in various specific manners as will now be apparent to those skilled in the art. Thus, for example, the instrumentation 11 can be machined out of stainless steel or the like.

The preferred method of sizing the end of a distal femur 13, of performing an anterior femoral resection 21 of the distal femur 13, and of performing a distal femoral resection 19 of the distal femur 13 starts with standard preoperative planning to estimate the size of the prosthesis to be implanted by, for example, comparing lateral radiographs of the distal femur 13 with implant templates, etc. The template size that most closely matches the profile of the distal femur 13 on the anterior and posterior aspect is normally chosen. In order to maintain proper quadriceps tension in flexion and extension, the patellar flange should not be radically shifted either anteriorly or posteriorly. The knee joint can then be exposed using a long anterior skin incision and medical parapatellar incision or the like. Any osteophytes should be removed from the intercondylar notch area of the distal aspect 19 of the distal femur 13 with a rongeur or the like to provide a clear view of the wails and roof of the intercondylar notch. An intramedullary cavity 135 can then be prepared in the distal aspect 19 of the distal femur 13, preferably with an entry point in the deepest point of the patellar groove just anterior to the cortical roof of the intercondylar notch. The intramedullary cavity 135 can be started with a pilot point drill and then finished with an intramedullary reamer or combination intramedullary reamer and intramedullary rod. In any event, the intramedullary rod 37 is then implanted into the intramedullary cavity 135 with the distal end 35 of the intramedullary rod 37 extending outward from the distal aspect 19 of the distal femur 13. The instrument body construct 25 is then assembled using a selected one of the valgus modules 61, 63, 65 based on the desired valgus angle. If full length extremity radiographs or films are available, the appropriate valgus angle may be estimated by the angle formed between the anatomical axis (the longitudinal axis of the femoral shaft) and the mechanical axis (a line extending through the centers of the femoral head, knee joint and angle joint). The valgus angle may also be determined by using an external alignment rod or the like. The desired valgus angle is set by merely mounting the appropriate one of the valgus modules 61, 63, 65 to the instrument body 27 using the lock nut 87, etc. The instrument body construct 25, with the selected valgus module 61, 63, 65, is positioned on the intramedullary rod 37 with the distal end 35 of the intramedullary rod 37 extending through the cavity 67 in the selected valgus module 61, 63, 65, and moved proximately until the planar face portion 30 of the distal aspect abutting surface 29 abuts the distal aspect 19 of the distal femur 13. The assembly is then adjusted until the pointed end 95 of the stylus 93 rests against a portion of the anterior aspect 23 of the distal femur 13 (e.g., preferably against the lateral anterior condyle). The anterior-to-posterior size of the end of the distal femur 13 can then be read from the scale 109. The anterior-to-posterior size thus read corresponds or relates to the proper implant size to be implanted which determines, in part, the thickness of the initial femoral resections. If the reading falls between two sizes, the smaller size is generally indicated.

The anterior feeler gauge 91 is then removed from the instrument body construct 25 and the resection guide 113 is attached to the instrument body construct 25 in the first position by, for example, sliding the T-slot 121 of the resection guide 113 into the T-flange 123 of the second body member 47 of the instrument body 27 and then tightening the lock screw 125 to lock the resection guide 113 to the second body member 47 of the instrument body 27. As indicated hereinabove, the slots 117, 119 may be automatically set at 3° of external rotation. Handles, bone clamps, nails or pins may be used to help hold the assembly firmly in place on the distal femur 13. The second body member 47 may include apertures 137, ears 139, etc., to coact with such Handles, bone clamps, nails or pins, etc. The anterior femoral resection 21 is then cut by passing the bone resection member 16 of the bone resection tool 15 through the appropriate slot 117, 119 of the body member 115 of the resection guide 113.

The resection guide 113 is then removed from the instrument body construct 25, turned up on end and mounted to the instrument body construct 25 in the second position using the pins 129, etc. The resection guide 113 may then adjusted for more or less resection if so desired. Bone clamps, nails or pins may be used to hold the resection guide 113 firmly in place on the distal femur 13. Thus, for example, the resection guide 113 can be securely pinned to the distal femur 13 by inserting one or more headless bone pins 141 or the like through apertures 143 in the body member 115 and into the distal femur 13 as shown in FIG. 18. The instrument body construct 25 and intramedullary rod 135 may then be removed from the distal femur 13. The thickness of the distal femoral resection 17 should be equal to the thickness replaced by the distal condyle of the implant unless special ligament problems dictate otherwise. For example, a significant flexion contracture may require one to three millimeters of additional distal femoral resection. Recurvatum may require one to three millimeters less distal femoral resection. The distal femoral resection 17 is then cut by passing the bone resection member 16 of the bone resection tool 15 through the appropriate slot 117, 119 of the body member 115 of the resection guide 113. Once the distal femoral resection 17 has been completed, the resection guide 113 can be removed from the distal femur 13 and various additional resections or cuts can be made including, for example, an anterior flange or condylar cut, an anterior bevel cut or cuts, a posterior cut or cuts, a posterior bevel cut or cuts, a patellar track groove cut, a posterior stabilized cut, etc., to prepare the distal femur 13 to receive a trial prosthesis, etc.

Although the present invention has been described and illustrated with respect to a preferred embodiment and a preferred use therefor, it is not to be so limited since modifications and changes can be made therein which are within the full intended scope of the invention.

I claim:

1. Instrumentation for use by a surgeon to size the end of a distal femur, and to guide a bone resection tool to resect the end of the distal femur; the instrumentation comprising:

(a) an instrument body construct including an instrument body and a valgus module for attachment to the instrument body; the instrument body construct having a distal aspect abutting surface with a planar face for abutting the distal aspect of a distal femur at a fixed angle to the longitudinal axis of the distal femur, having a posterior aspect abutting surface with a planar face for abutting the posterior aspect of the distal femur, and having a passageway therethrough;

(b) an anterior feeler gauge attachable to the instrument body construct for contacting a portion of the anterior aspect of the distal femur; and (c) a resection guide attachable to the instrument body construct for guiding a bone resection tool to resect the distal femur; the resection guide including a body member having a slot therethrough for guiding the bone resection tool to perform a resection of the distal femur; the body member of the resection guide is attachable to the instrument body construct in a first position to orient the slot therethrough to guide the bone resection tool to perform an anterior femoral resection of the end of the distal femur and is attachable to the instrument body construct in a second position to orient the slot therethrough to guide the bone resection tool to perform a distal femoral resection of the end of the distal femur.

2. Instrumentation for use by a surgeon in combination with an intramedullary rod to size the end of a distal femur, and to guide a bone resection tool to perform an anterior femoral resection of the end of the distal femur and a distal femoral resection of the end of the distal femur; the instrumentation comprising:

(a) an instrument body construct including an instrument body and a valgus module for attachment to the instrument body; the instrument body construct having a distal aspect abutting surface with a planar face for abutting the distal aspect of a distal femur, having a posterior aspect abutting surface with a planar face for abutting the posterior aspect of the distal femur, and having a passageway therethrough for receiving the distal end of an intramedullary rod to position the planar face of the distal aspect abutting surface at a fixed angle to the longitudinal axis of the intramedullary rod;

(b) an anterior feeler gauge attachable to the instrument body construct for contacting a portion of the anterior aspect of the distal femur; and (c) a resection guide attachable to the instrument body construct for guiding a bone resection tool to perform an anterior femoral resection of the anterior aspect of the distal femur and a distal femoral resection of the distal aspect of the distal femur; the resection guide including a body member having a slot therethrough for guiding the bone resection tool to perform a resection of the distal femur; the body member of the resection guide is attachable to the instrument body construct in a first position to orient the slot therethrough to guide the bone resection tool to perform an anterior femoral resection of the end of the distal femur and is attachable to the instrument body construct in a second position to orient the slot therethrough to guide the bone resection tool to perform a distal femoral resection of the end of the distal femur.

3. The instrumentation of claim 2 in which the instrument body includes a first body member having a first end and a second end with the posterior aspect abutting surface attached to and extending outward from the first end of the first body member; and in which the instrument body includes a second body member having a first end and a second end with the anterior feeler gauge attached to the second end of the second body member; the first and second body members are slidably joined to one another to allow the posterior aspect abutting surface and the anterior feeler gauge to be moved toward and away from one another.

4. The instrumentation of claim 2 in which the valgus module has a flange; in which the instrument body has a groove therein for slidably receiving the flange of the valgus module to slidably join the valgus module to the instrument body; and in which is included a lock member for locking the valgus module to the instrument body.

5. The instrumentation of claim 4 in which a portion of the valgus module is threaded and in which the lock member includes a lock nut for threadably engaging the threaded portion of the valgus module.

6. The instrumentation of claim 2 in which the passageway through the instrument body construct has a longitudinal axis that forms an angle with a plane that is substantially perpendicular to the planar face portion of the distal aspect abutting surface of the instrument body construct substantially within the range of ±15°.

7. A method of sizing the end of a distal femur, of performing an anterior femoral resection of the distal femur, and of performing a distal femoral resection of the distal femur; the method comprising the steps of:

(a) implanting an intramedullary rod in the distal femur with the distal end of the intramedullary rod extending from the distal femur;

(b) providing instrumentation including an anterior feeler gauge, a resection guide, and an instrument body construct including an instrument body and a valgus module for attachment to the instrument body; the instrument body construct having a distal aspect abutting surface with a planar face for abutting the distal aspect of a distal femur, having a posterior aspect abutting surface with a planar face for abutting the posterior aspect of the distal femur, and having a passageway therethrough for receiving the distal end of an intramedullary rod to position the planar face of the distal aspect abutting surface at a fixed angle to the longitudinal axis of the intramedullary rod;

(c) inserting the passageway of the valgus module over the distal end of the intramedullary rod until the distal aspect abutting surface of the instrument body abuts the distal aspect of the distal femur;

(d) mounting the anterior feeler gauge on the instrument body construct;

(e) adjusting the instrument body construct and anterior feeler gauge until the posterior aspect abutting surface of the instrument body construct abuts the posterior aspect of the distal femur and until the anterior feeler gauge engages the anterior aspect of the distal femur;

(f) mounting the resection guide on the instrument body construct in a first position and using the resection guide to guide a bone resection tool to perform an anterior femoral resection of the distal femur; and (g) mounting the resection guide on the instrument body construct in a second position and using the resection guide to guide the bone resection tool to perform a distal femoral resection of distal femur.

8. Instrumentation for use by a surgeon in combination with an intramedullary rod to guide a bone resection tool to perform an anterior femoral resection of the end of the distal femur and a distal femoral resection of the end of the distal femur; the instrumentation comprising:

(a) an instrument body construct having a distal aspect abutting surface with a planar face for abutting the distal aspect of a distal femur, having a posterior aspect abutting surface with a planar face for abutting the posterior aspect of the distal femur, and having a passageway therethrough receiving the distal end of the intramedullary rod to position the planar face of the distal aspect abutting surface at a fixed angle to the longitudinal axis of the intramedullary rod; and (b) a resection guide attachable to the instrument body construct for guiding a bone resection tool to perform an anterior femoral resection of the anterior aspect of the distal femur and a distal femoral resection of the distal aspect of the distal femur; the resection guide including a body member having a slot therethrough for guiding the bone resection tool to perform a resection of the distal femur; the body member of the resection guide is attachable to the instrument body construct in a first position to orient the slot therethrough to guide the bone resection tool to perform an anterior femoral resection of the end of the distal femur and is attachable to the instrument body construct in a second position to orient the slot therethrough to guide the bone resection tool to perform a distal femoral resection of the end of the distal femur.

* * * * *